United States Patent
Freeberg et al.

(10) Patent No.: US 7,813,799 B2
(45) Date of Patent: Oct. 12, 2010

(54) ADAPTIVE SAFETY PACING

(75) Inventors: Scott M. Freeberg, White Bear Lake, MN (US); Michael J. Lyden, Shoreview, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1341 days.

(21) Appl. No.: 10/952,345

(22) Filed: Sep. 28, 2004

(65) Prior Publication Data
US 2005/0137640 A1 Jun. 23, 2005

Related U.S. Application Data

(60) Provisional application No. 60/527,780, filed on Dec. 8, 2003.

(51) Int. Cl.
*A61N 1/362* (2006.01)
(52) U.S. Cl. .................... 607/28; 607/9
(58) Field of Classification Search ............ 607/28, 607/9, 11, 12, 141
See application file for complete search history.

(56) References Cited

U.S. PATENT DOCUMENTS

| 5,222,493 | A | | 6/1993 | Sholder | |
|---|---|---|---|---|---|
| 5,391,192 | A | * | 2/1995 | Lu et al. | 607/28 |
| 5,766,230 | A | * | 6/1998 | Routh et al. | 607/27 |
| 6,128,535 | A | | 10/2000 | Maarse | |
| 6,456,871 | B1 | | 9/2002 | Hsu et al. | |
| 6,456,882 | B1 | * | 9/2002 | Schloss | 607/28 |
| 6,473,649 | B1 | * | 10/2002 | Gryzwa et al. | 607/28 |
| 6,697,673 | B1 | * | 2/2004 | Lu | 607/28 |
| 7,035,687 | B1 | * | 4/2006 | Levine et al. | 607/28 |

* cited by examiner

*Primary Examiner*—Carl H Layno
*Assistant Examiner*—Brian T Gedeon
(74) *Attorney, Agent, or Firm*—Hollingsworth & Funk, LLC (57) ABSTRACT

Methods and systems involve adjusting an energy used for safety pacing based on the capture threshold. The safety pacing energy may be adjusted prior to a capture threshold test. During the capture threshold test, backup safety paces are delivered using the adjusted pacing energy. Following suspension of automatic capture verification, the device may enter a suspension mode. During the suspension mode, safety pacing pulses are delivered using a pacing energy adjusted based on capture threshold.

26 Claims, 5 Drawing Sheets

ADAPTIVE SAFETY PACING

RELATED PATENT DOCUMENTS

This application claims the benefit of Provisional Patent Application Ser. No. 60/527,780, filed on Dec. 8, 2003, to which priority is claimed pursuant to 35 U.S.C. §119(e) and which is hereby incorporated herein by reference.

FIELD OF THE INVENTION

The present invention relates generally to implantable medical devices and, more particularly, to implantable cardiac devices and methods for adaptively altering safety pacing.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into the patient's heart are connected to electrodes that contact the myocardium for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management devices that deliver a series of low energy pace pulses timed to assist the heart in producing a contractile rhythm that maintains cardiac pumping efficiency. Pace pulses may be intermittent or continuous, depending on the needs of the patient.

When a pace pulse produces a contraction in the heart tissue, the electrical cardiac signal following the contraction is denoted the captured response. A pace pulse must exceed a minimum energy value, or capture threshold, to produce a contraction. The capture threshold is defined as the lowest pacing energy that consistently captures the heart. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

For the reasons stated above, and for other reasons stated below which will become apparent to those skilled in the art upon reading the present specification, there is a need in the art for methods and systems for automatically adjusting the pacing energy for pacing pulses delivered to the patient. The present invention fulfills these and other needs.

SUMMARY OF THE INVENTION

Embodiments of the invention are directed to methods and systems for adjusting an energy used for safety pacing pulses. One embodiment of the invention involves a method for delivering safety pacing to a patient. The method includes determining a capture threshold and adjusting the safety pacing energy based on the capture threshold.

In accordance with one aspect of the invention, adjustment of the safety pacing energy involves safety paces delivered during a capture threshold test. In accordance with another aspect, adjustment of the safety pacing energy involves safety pacing pulses delivered when the device is operating in a suspension mode after automatic capture verification has been suspended. Adjustment of the safety pacing energy may involve adjusting the energy for safety pacing during automatic capture verification suspension to a predetermined amount above the capture threshold.

Another embodiment of the invention is directed to a medical device for delivering cardiac pacing therapy to a patient. The medical device includes a plurality of electrodes configured to electrically couple to a heart and to deliver pacing pulses to a heart. Detection circuitry is coupled to the electrodes and is configured to determine a capture threshold energy associated with the pacing pulses. The medical device also includes a pulse generator coupled to the plurality of electrodes and the detection circuitry. The pulse generator is configured to adjust an energy for safety pacing based on the capture threshold energy.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

The present invention involves methods and systems for adjusting the energy of safety pacing pulses. The safety pacing pulses comprise, for example, safety backup pacing pulses delivered following the primary pulses of a capture verification test and safety pacing pulses delivered after automatic capture verification is suspended. In accordance with various embodiments described herein, the energy of the safety pacing pulses is adjusted based on previously acquired capture threshold information.

Figure 1:
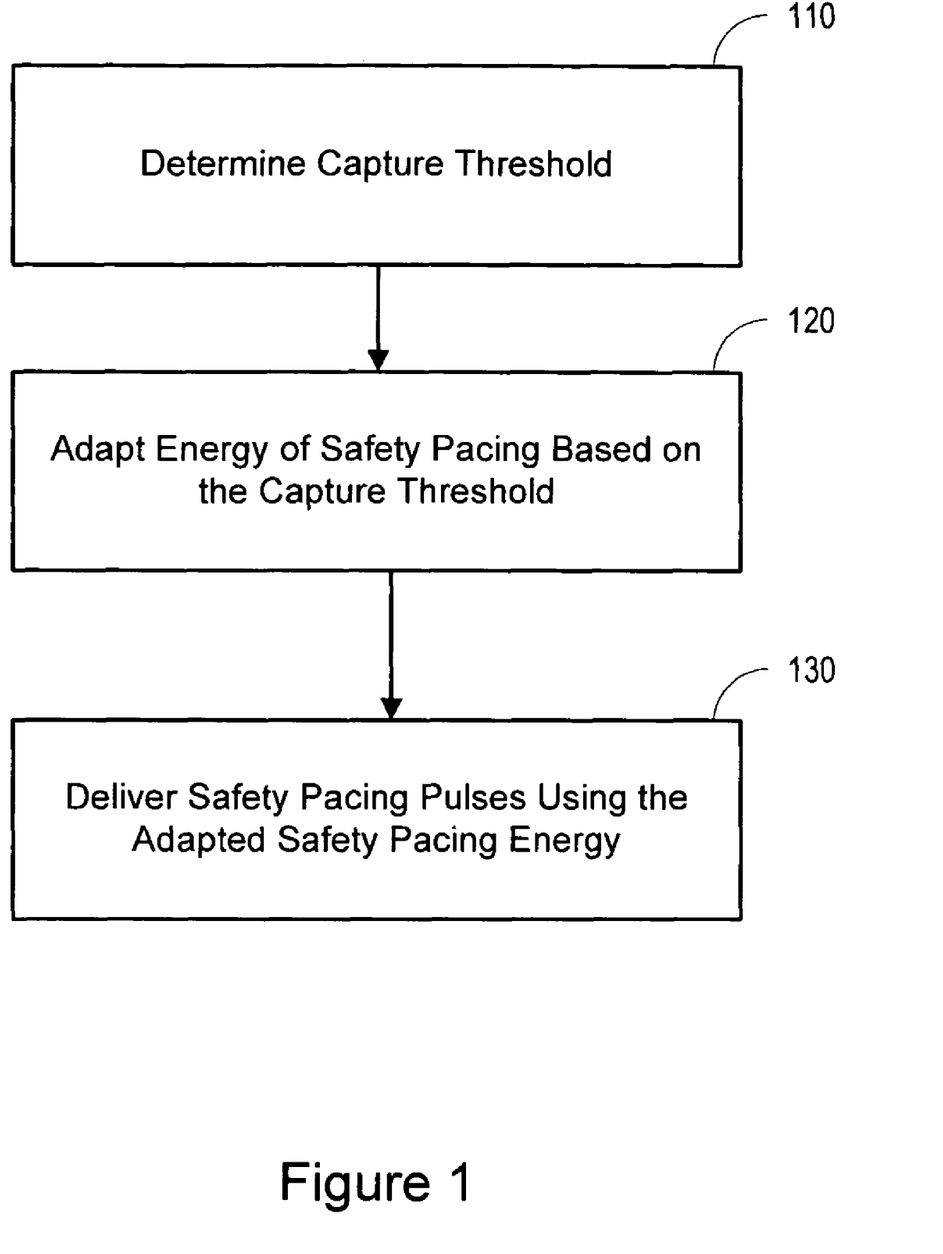
FIG. 1 is a flowchart of an adaptive safety pacing method in accordance with embodiments of the present invention.

FIG. 1 illustrates a method of adjusting the safety pacing energy in accordance with embodiments of the invention. The capture threshold is determined 110, for example, through an automatic capture threshold testing procedure. The safety pacing energy is adjusted 120 based on the capture threshold. The capture threshold of one heart chamber may be used to adjust the safety pacing energy of another heart chamber. For example, the system may determine the capture threshold of a first heart chamber, e.g., the right ventricle. The safety pacing energy of a second heart chamber, e.g., the left ventricle, may be adjusted based on the capture threshold of the first heart chamber.

Safety pacing pulses may be delivered 130, for example during a capture threshold test or after suspension of an automatic capture verification feature.

Capture threshold tests are typically used to determine the capture threshold. During the capture threshold test the pacing energy is stepped down until loss of capture is detected. Safety backup paces follow the primary paces of a capture threshold test to ensure that there is no interruption in therapy. Capture threshold testing may occur once an hour or once a day, for example.

Those skilled in the art will appreciate that reference to a capture threshold procedure indicates a method of determining the capture threshold in one of left atrium, right atrium, left ventricle, right ventricle, or in any combination of heart chambers, e.g., left and right atria and/or left and right ventricles. In such a procedure, the pacemaker, automatically or upon command, initiates a search for the capture threshold of the selected heart chamber or chambers.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. The pacemaker may increase the stimulation energy in discrete steps until a predetermined number of capture events occur to confirm the capture threshold. A capture threshold test may be performed using adaptive safety back up pacing methods of the present invention.

Other procedures for implementing capture threshold testing may be utilized. In one example, the pacing energy may be increased in discrete steps until capture is detected. In another example, the pacing energy may be adjusted according to a binomial search pattern.

Automatic capture threshold determination is distinguishable from automatic capture verification, a procedure that may occur on a beat-by-beat basis during pacing. Automatic capture verification verifies that a delivered pace pulse results in a captured response. When a captured response is not detected following a pace pulse, the pacemaker may deliver a back up safety pacing pulse to ensure consistent pacing. The back up safety pace may be delivered, for example, about 70-80 ms after the initial pace pulse. If a predetermined number of pace pulses delivered during normal pacing do not produce a captured response, the pacemaker may initiate several optional features. According to one optional feature, for example, if loss of capture is detected, the pacemaker may schedule a capture threshold test to re-evaluate the capture threshold. Alternatively or additionally, the pacemaker may suspend automatic capture verification and revert to a safety pacing protocol that involves delivering pacing pulses at an energy level that ensures capture and avoids interruption of pacing therapy.

The embodiments of the present system illustrated herein are generally described as being implemented in an implantable cardiac defibrillator (ICD) that may operate in numerous pacing modes known in the art. Various types of single and multiple chamber implantable cardiac defibrillators are known in the art and may be used in connection with the adaptive safety back up pacing methods of the present invention. The methods of the present invention may also be implemented a variety of implantable or patient-external cardiac rhythm management devices, including single and multi chamber pacemakers, defibrillators, cardioverters, bi-ventricular pacemakers, and cardiac resynchronizers, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 2:
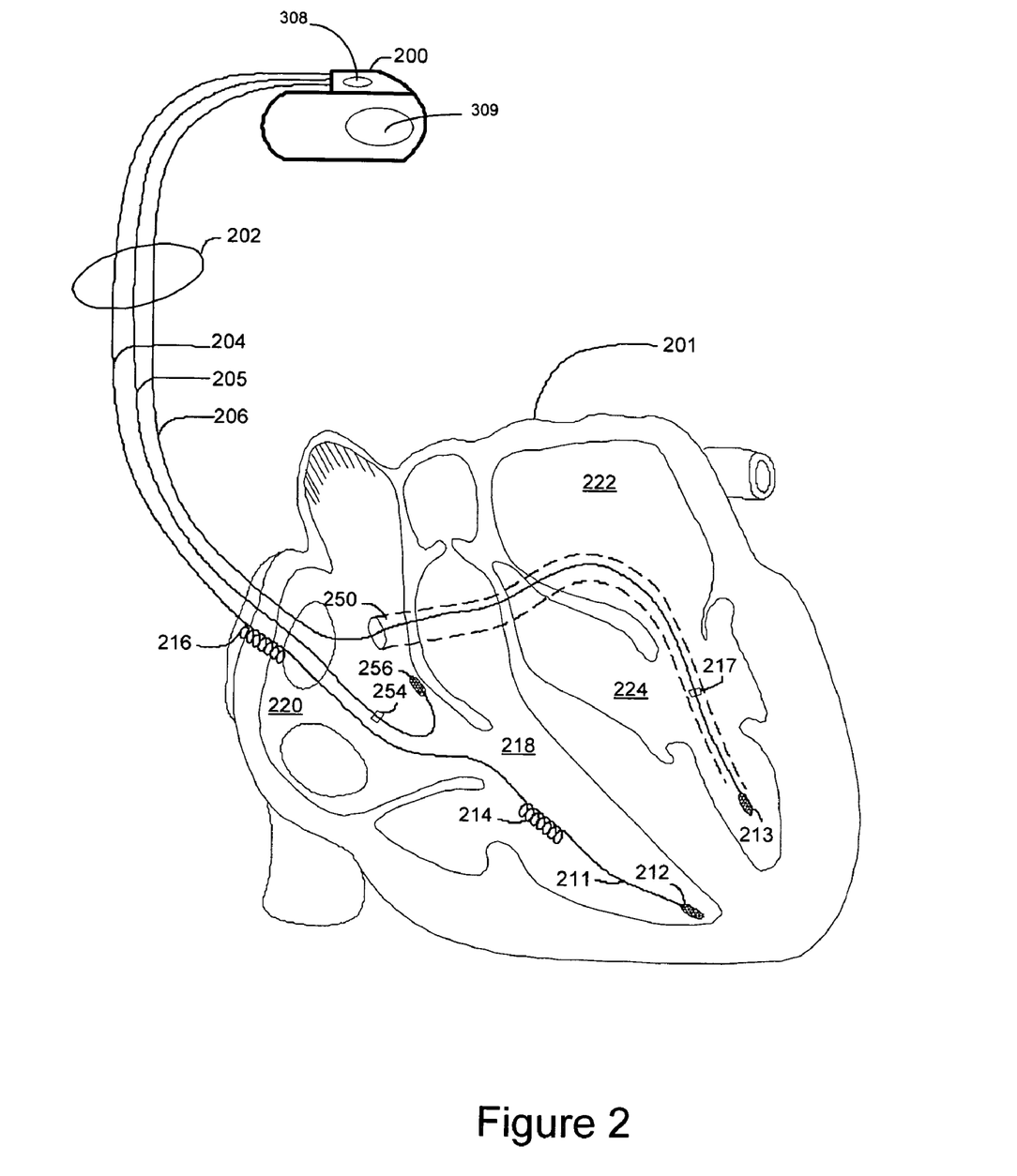
FIG. 2 is a partial view of an implantable medical device in accordance with embodiments of the invention.

Referring now to FIG. 2 of the drawings, there is shown a cardiac rhythm management system that may be used to implement adaptive safety back up pacing methods of the present invention. The cardiac rhythm management system in FIG. 2 includes an ICD 200 electrically and physically coupled to a lead system 202. The housing and/or header of the ICD 200 may incorporate a can electrode 309 used to provide electrical stimulation energy to the heart and to sense cardiac electrical activity. The ICD 200 may utilize all or a portion of the ICD housing as a can electrode 309.

The lead system 202 is used to detect electric cardiac signals produced by the heart 201 and to provide electrical energy to the heart 201 under certain predetermined conditions to treat cardiac arrhythmias. The lead system 202 may include one or more electrodes used for pacing, sensing, and/or defibrillation. In the embodiment shown in FIG. 2, the lead system 202 includes an intracardiac right ventricular (RV) lead system 204, an intracardiac right atrial (RA) lead system 205, an intracardiac left ventricular (LV) lead system 206. The lead system 202 of FIG. 2 illustrates one embodiment that may be used in connection with the adaptive safety back up pacing methodologies described herein. Other leads and/or electrodes may additionally or alternatively be used.

The lead system 202 may include intracardiac leads 204, 205, 206 implanted in a human body with portions of the intracardiac leads 204, 205, 206 inserted into a heart 201. The intracardiac leads 204, 205, 206 include various electrodes positionable within the heart for sensing electrical activity of the heart and for delivering electrical stimulation energy to the heart, for example, pacing pulses and/or defibrillation shocks to treat various arrhythmias of the heart.

Other configurations of endocardial leads and electrodes are possible and are considered to be included within the scope of the invention. The other configurations of endocardial leads and electrodes may be used to implement sensing and/or pacing in any one or more of the right atrium, right ventricle, left atrium and left ventricle. Although not illustrated in FIG. 2, the lead system 202 may additionally or alternatively include one or more extracardiac leads having electrodes, e.g., epicardial electrodes, positioned at locations outside the heart for sensing and pacing one or more heart chambers including any one or more of the right atrium, right ventricle, left atrium and left ventricle.

The right ventricular lead system 204 illustrated in FIG. 2 includes an SVC-coil 216, an RV-coil 214, an RV-ring electrode 211, and an RV-tip electrode 212. The right ventricular lead system 204 extends through the right atrium 220 and into the right ventricle 218. In particular, the RV-tip electrode 212, RV-ring electrode 211, and RV-coil electrode 214 are positioned at appropriate locations within the right ventricle 218 for sensing and delivering electrical stimulation pulses to the heart. The SVC-coil 216 is positioned at an appropriate location within the right atrium chamber 220 of the heart 201 or a major vein leading to the right atrial chamber 220 of the heart 201.

In one configuration, the RV-tip electrode 212 referenced to the can electrode 309 may be used to implement unipolar pacing and/or sensing in the right ventricle 219. Bipolar pacing and/or sensing in the right ventricle may be implemented using the RV-tip 212 and RV-ring 211 electrodes. In yet another configuration, the RV-ring 211 electrode may optionally be omitted, and bipolar pacing and/or sensing may be accomplished using the RV-tip electrode 212 and the RV-coil 214, for example. The right ventricular lead system 204 may be configured as an integrated bipolar pace/shock lead. The RV-coil 214 and the SVC-coil 216 are defibrillation electrodes.

The left ventricular lead 206 includes an LV distal electrode 213 and an LV proximal electrode 217 located at appropriate locations in or about the left ventricle 224 for pacing and/or sensing the left ventricle 224. The left ventricular lead 206 may be guided into the right atrium 220 of the heart via the superior vena cava. From the right atrium 220, the left ventricular lead 206 may be deployed into the coronary sinus ostium, the opening of the coronary sinus 250. The lead 206 may be guided through the coronary sinus 250 to a coronary vein of the left ventricle 224. This vein is used as an access pathway for leads to reach the surfaces of the left ventricle 224 which are not directly accessible from the right side of the heart. Lead placement for the left ventricular lead 206 may be achieved via subclavian vein access and a preformed guiding catheter for insertion of the LV electrodes 213, 217 adjacent to the left ventricle.

Unipolar pacing and/or sensing in the left ventricle may be implemented, for example, using the LV distal electrode referenced to the can electrode 309. The LV distal electrode 213 and the LV proximal electrode 217 may be used together as bipolar sense and/or pace electrodes for the left ventricle. The left ventricular lead 206 and the right ventricular lead 204, in conjunction with the ICD 200, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 205 includes a RA-tip electrode 256 and an RA-ring electrode 254 positioned at appropriate locations in the right atrium 220 for sensing and pacing the right atrium 220. In one configuration, the RA-tip 256 referenced to the can electrode 309, for example, may be used to provide unipolar pacing and/or sensing in the right atrium 220. In another configuration, the RA-tip electrode 256 and the RA-ring electrode 254 may be used to effect bipolar pacing and/or sensing.

Figure 3:
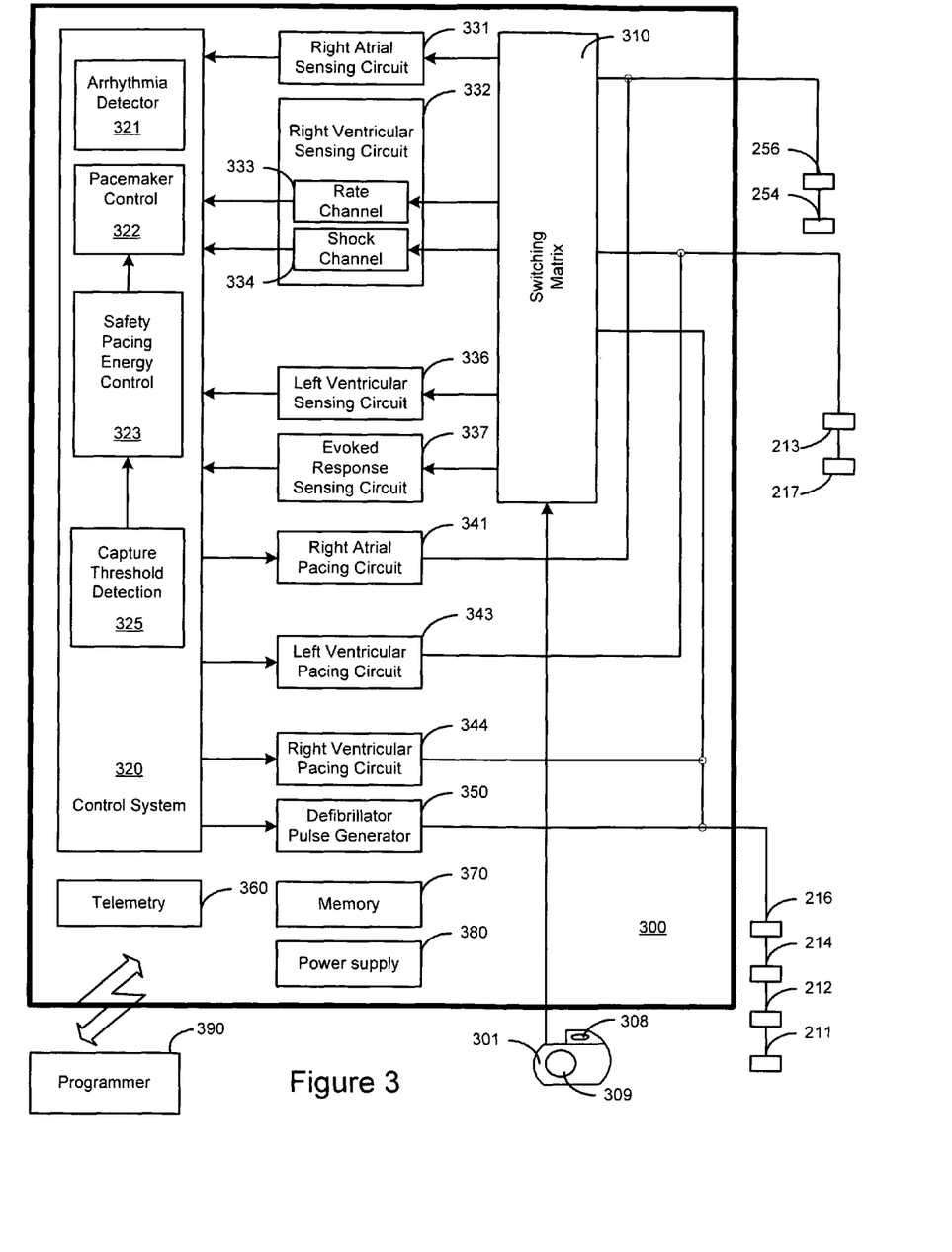
FIG. 3 is a block diagram of an implantable medical device in accordance with embodiments of the invention.

Referring now to FIG. 3, there is shown an embodiment of a cardiac defibrillator 300 suitable for implementing an adaptive safety back up pacing methodology of the present invention. FIG. 3 shows a cardiac defibrillator divided into functional blocks. It is understood by those skilled in the art that there exist many possible configurations in which these functional blocks can be arranged. The example depicted in FIG. 3 is one possible functional arrangement. Other arrangements are also possible. For example, more, fewer or different functional blocks may be used to describe a cardiac defibrillator suitable for implementing the adaptive safety back up pacing methodology of the present invention. In addition, although the cardiac defibrillator 300 depicted in FIG. 3 contemplates the use of a programmable microprocessor-based logic circuit, other circuit implementations may be utilized.

The cardiac defibrillator 300 depicted in FIG. 3 includes circuitry for receiving cardiac signals from a heart and delivering electrical stimulation energy to the heart in the form of pacing pulses or defibrillation shocks. In one embodiment, the circuitry of the cardiac defibrillator 300 is encased and hermetically sealed in a housing 301 suitable for implanting in a human body. Power to the cardiac defibrillator 300 is supplied by an electrochemical battery 380. A connector block (not shown) is attached to the housing 301 of the cardiac defibrillator 300 to allow for the physical and electrical attachment of the lead system conductors to the circuitry of the cardiac defibrillator 300.

The cardiac defibrillator 300 may be a programmable microprocessor-based system, including a control system 320 and a memory 370. The memory 370 may store parameters for various pacing, defibrillation, and sensing modes, along with other parameters such as capture threshold information. Further, the memory 370 may store data indicative of cardiac signals received by other components of the cardiac defibrillator 300. The memory 370 may be used, for example, for storing historical EGM and therapy data. The historical data storage may include, for example, data obtained from long term patient monitoring used for trending or other diagnostic purposes. Historical data, as well as other information, may be transmitted to an external programmer unit 390 as needed or desired.

The control system 320 and memory 370 may cooperate with other components of the cardiac defibrillator 300 to control the operations of the cardiac defibrillator 300. The control system depicted in FIG. 3 incorporates a processor 325 for classifying cardiac responses to pacing stimulation and safety pacing protocols in accordance with various embodiments of the present invention. The control system 320 may include additional functional components including a pacemaker control circuit 322, an arrhythmia detector 321, capture threshold detection circuitry 325, safety pacing energy control circuitry 323, along with other components for controlling the operations of the cardiac defibrillator 300.

Telemetry circuitry 360 may be implemented to provide communications between the cardiac defibrillator 300 and an external programmer unit 390. In one embodiment, the telemetry circuitry 360 and the programmer unit 390 communicate using a wire loop antenna and a radio frequency telemetric link, as is known in the art, to receive and transmit signals and data between the programmer unit 390 and the telemetry circuitry 360. In this manner, programming commands and other information may be transferred to the control system 320 of the cardiac defibrillator 300 from the programmer unit 390 during and after implant. In addition, stored cardiac data pertaining to capture threshold, capture detection and/or adaptive safety back up pacing, for example, along with other data, may be transferred to the programmer unit 390 from the cardiac defibrillator 300.

In the embodiment of the cardiac defibrillator 300 illustrated in FIG. 3, electrodes RA-tip 256, RA-ring 254, RV-tip 213, RV-ring 211, RV-coil, SVC-coil, LV distal electrode 213, LV proximal electrode 217, and can electrode 309 are coupled through a switch matrix 310 to sensing circuits 331, 332, 336, and 337.

A right atrial sensing circuit 331 serves to detect and amplify electrical signals from the right atrium of the heart. Bipolar sensing in the right atrium may be implemented, for example, by sensing voltages developed between the RA-tip 256 and the RA-ring 254. Unipolar sensing may be implemented, for example, by sensing voltages developed between the RA-tip 256 and the can electrode 309. Outputs from the right atrial sensing circuit are coupled to the control system 320.

A right ventricular sensing circuit 332 serves to detect and amplify electrical signals from the right ventricle of the heart. The right ventricular sensing circuit 332 may include, for example, a right ventricular rate channel 333 and a right ventricular shock channel 334. Right ventricular cardiac signals sensed through use of the RV-tip 213 electrode are right ventricular near-field signals and are denoted RV rate channel signals. A bipolar RV rate channel signal may be sensed as a voltage developed between the RV-tip 213 and the RV-ring. Alternatively, bipolar sensing in the right ventricle may be implemented using the RV-tip electrode 213 and the RV-coil 214. Unipolar rate channel sensing in the right ventricle may be implemented, for example, by sensing voltages developed between the RV-tip 213 and the can electrode 309.

Right ventricular cardiac signals sensed through use of defibrillation electrodes 214, 216, 309 are far-field signals, also referred to as RV morphology or RV shock channel signals. More particularly, a right ventricular shock channel signal may be detected as a voltage developed between the RV-coil 214 and the SVC-coil 216. A right ventricular shock channel signal may also be detected as a voltage developed between the RV-coil 214 and the can electrode 309. In another configuration the can electrode 309 and the SVC-coil electrode 216 may be electrically shorted and a RV shock channel signal may be detected as the voltage developed between the RV-coil 214 and the can electrode 309/SVC-coil 216 combination.

Outputs from the right ventricular sensing circuit 332 are coupled to the control system 320. Cardiac signals sensed using one or both of the rate channel 333 and the shock channel 334 sensing amplifies may be used by the arrhythmia detector 321 to detect arrhythmic cardiac rhythms.

A left ventricular sensing circuit 336 serves to detect and amplify electrical signals from the left ventricle of the heart. Bipolar sensing in the left ventricle may be implemented, for example, by sensing voltages developed between the LV distal electrode 213 and the LV proximal electrode 217. Unipolar sensing may be implemented, for example, by sensing voltages developed between the LV distal electrode 213 or the LV proximal electrode 217 to the can electrode 309. Signals detected using combinations of the LV electrodes, 213, 217, and/or can 309 electrodes may be sensed and amplified by the left ventricular sensing circuitry 336. The output of the left ventricular sensing circuit 336 is coupled to the control system 320.

The outputs of the switching matrix 310 may be operated to couple selected combinations of electrodes 211, 212, 213, 214, 216, 217, 256, 254 to the captured response sensing circuit 337. The captured response sensing circuit 337 serves to sense and amplify voltages developed using various combinations of electrodes. Signals sensed by the captured response sense circuit 337 are used by the capture threshold detector to determine capture thresholds associated with various electrode configurations.

Capture threshold information acquired by the capture threshold detection circuit 325 may be used by the safety pacing energy controller to control the energy of safety pacing pulses delivered to the heart. According to one embodiment, safety pacing pulses may be delivered using the adapted safety pacing energy after each of the primary pacing pulses of a capture threshold test. According to another embodiment, safety pacing pulses may be delivered using the adapted safety pacing energy following suspension of automatic capture verification.

Embodiments of the invention are directed to adjusting the safety pacing energy if automatic capture verification is suspended. Conventional approaches pace at a set high pacing energy upon suspension of automatic capture verification. The high pacing energy utilized by conventional approaches may decrease battery lifetime and/or cause patient discomfort.

To mitigate pacing discomfort and decreased battery life caused by using an arbitrary high pacing energy during automatic capture verification suspension, the embodiments described herein utilize an algorithm that automatically adjusts and applies an appropriately lower pacing amplitude. Pacing discomfort can arise during RA or RV unipolar pacing if pace pulse energy is high enough that anodal stimulation of muscle proximal to the pulse generator case occurs. Similarly, LV pacing can cause patient discomfort if the pace energy is high enough that the phrenic nerve is stimulated.

The pacing amplitude is determined based on pacing threshold history. In some embodiments, the adjusted pacing amplitude varies linearly with capture threshold within a fixed range. Regardless of the calculation, the pacing amplitude may be subject to minimum and maximum limits. If recent or current capture threshold tests indicate low pacing thresholds, the algorithm will apply a lower suspension mode pacing amplitude rather than an arbitrary fixed amplitude as in conventional approaches. If recent or current capture threshold tests indicate a higher pacing threshold, the algorithm will apply an appropriately higher suspension pacing amplitude based on capture thresholds measured prior to entering suspension mode.

Figure 4:
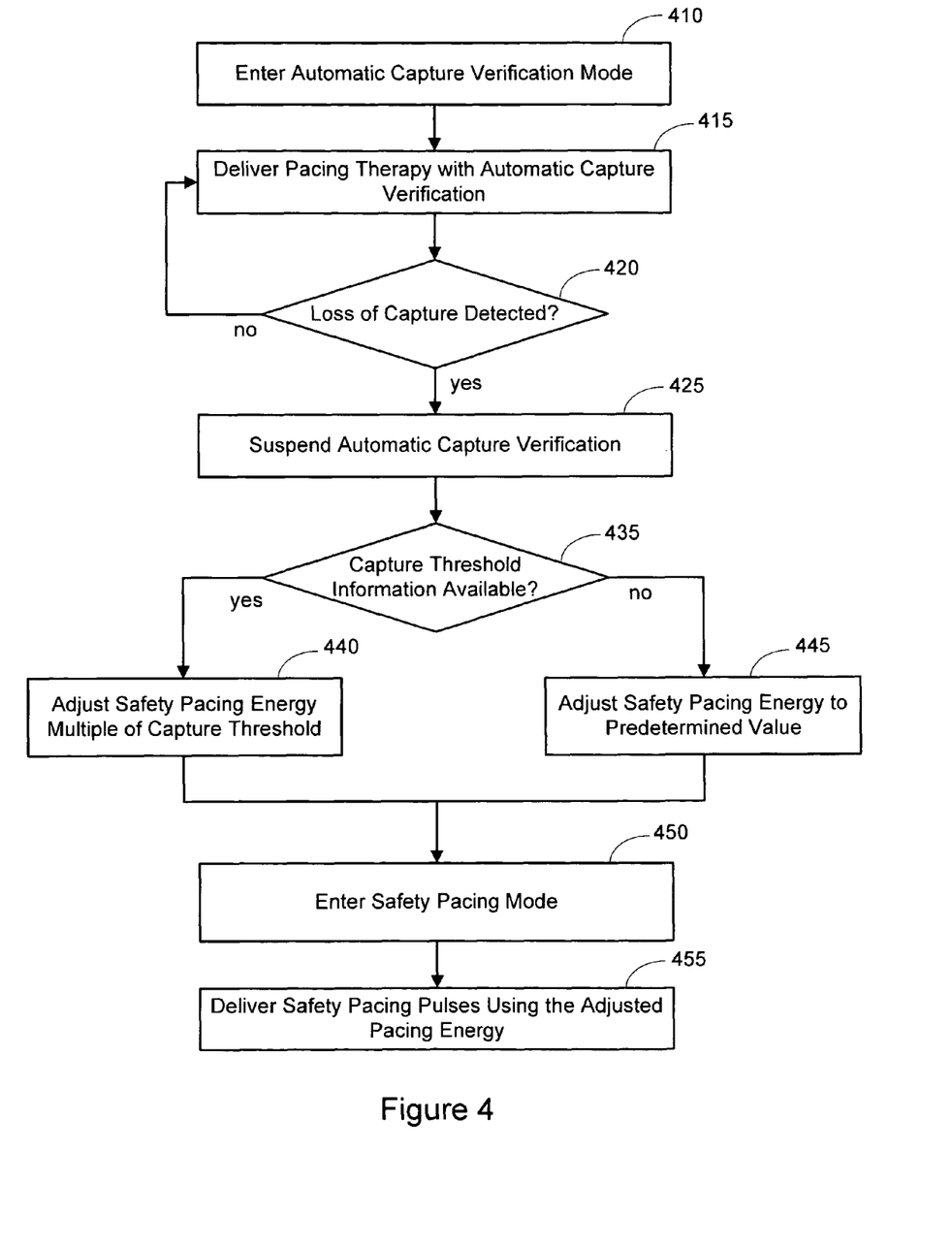
FIG. 4 is a flowchart illustrating a method for delivering safety pacing upon suspension of automatic capture verification in accordance with embodiments of the invention.

FIG. 4 is a flowchart illustrating a method for delivering safety pacing upon suspension of automatic capture verification in accordance with embodiments of the invention. When operating 410 in automatic capture verification mode, the pacemaker delivers 415 scheduled pacing pulses and automatically determines if the pacing pulses capture the heart. If a sufficient number of pacing pulses do not produce capture, for example, about 4 out of about 6 beats, the pacemaker may detect 420 loss of capture.

If loss of capture is detected 420, the pacemaker suspends 425 automatic capture verification. If capture threshold information is available 435 and was recently measured, for example, within about 24 hours, then the recently acquired capture threshold is used to adjust 440 the safety pacing energy. In one implementation, the safety pacing energy is adjusted to be a multiple of the capture threshold, for example, twice the capture threshold.

In some implementations, the adjustment of the pacing energy is subject to a minimum value, for example, about 3.5 volts, and a maximum value, for example, about 5 volts. In cases where the capture threshold is low, such as less than about 1 volt, the suspension mode pacing voltage would be set to a minimum value, such as about 3.5 volts. In cases wherein the capture threshold is higher, such as approaching about 2.5 volts, the pacing voltage would be set to a maximum value, such as about 5 volts.

If capture threshold information is not available 435 or was not recently measured, then the pacing energy for the safety pacing mode is adjusted 445 to a predetermined value, for example about 5 volts.

After adjustment 440, 445 of the pacing energy, the pacemaker enters 450 safety pacing mode. During safety pacing mode, beat-by-beat capture verification no longer occurs. Pacing pulses are delivered 455 using the adjusted safety pacing energy.

It may be possible that some patients may have automatic capture verification suspended for long periods of time depending on the patient's suitability to automatic capture verification. The intelligent safety pacing adjustment algorithm described herein will lessen the negative impact of automatic capture verification suspension on battery life. Further, using adaptive safety pacing adjustment will reduce patient discomfort associated with high pacing energies.

Figure 5:
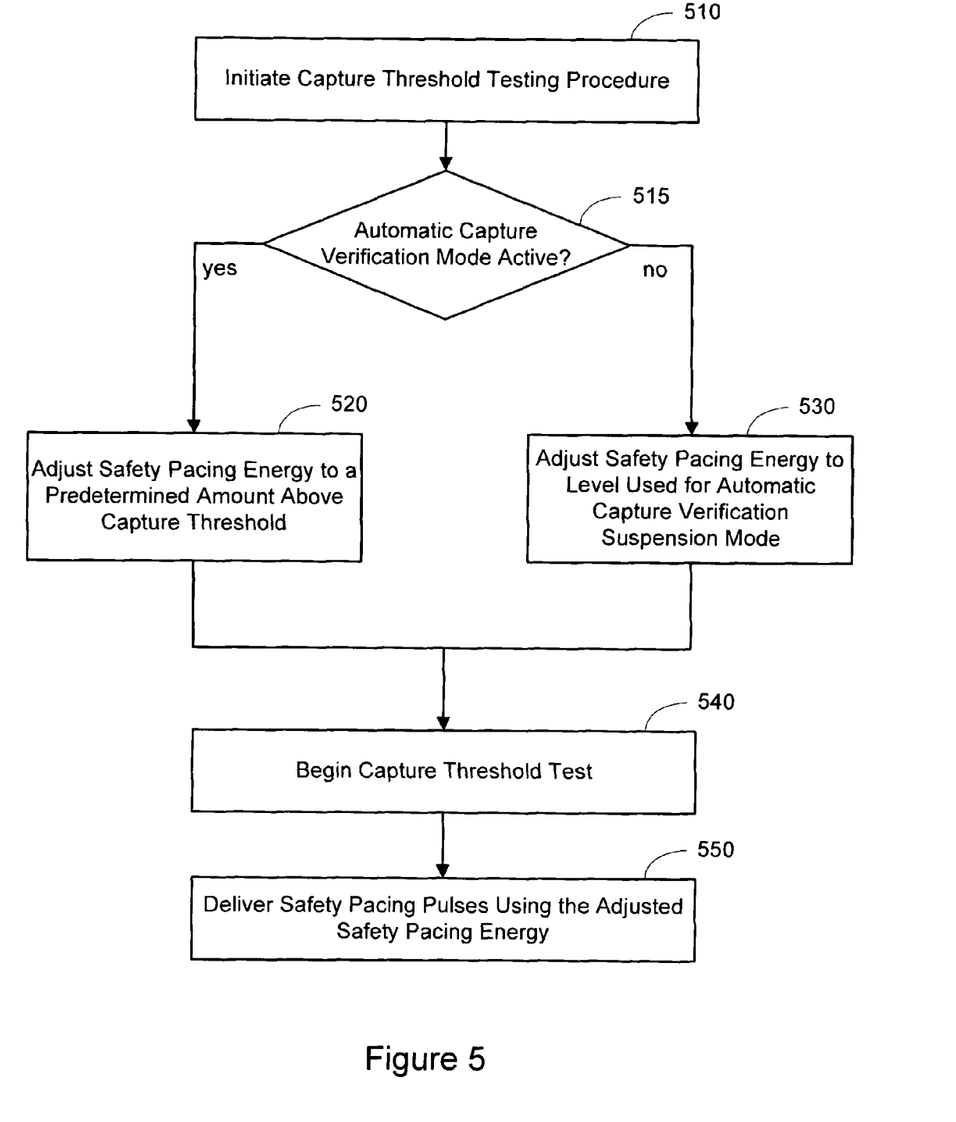
FIG. 5 is a flowchart illustrating a method of performing a capture threshold test using an adjustable safety pacing energy in accordance with embodiments of the invention.

FIG. 5 is a flowchart illustrating a method of performing a capture threshold test using an adjustable safety pacing energy in accordance with embodiments of the invention. Upon initiation 510 of a capture threshold test procedure, the system determines if automatic capture verification is active 515. If automatic capture verification is active 515 at the start of the capture threshold test procedure, then the safety pacing energy may be adjusted 520 to a predetermined amount above the capture threshold. For example the safety pacing voltage may be set to about 1.5 volts above the measured capture threshold. If the adjusted safety pacing voltage is below a minimum value, such as about 3.5 volts, the safety pacing voltage may be set to the minimum value. If the adjusted safety pacing voltage is above a maximum value, such as about 5 volts, the safety pacing voltage may be set to the maximum value.

If automatic capture verification mode is not active 515, then the safety pacing energy is adjusted 530 to the energy level used for automatic capture verification suspension mode. The capture threshold test begins 540 during which safety pacing pulses are delivered 550 using the adjusted pacing energy.

The safety pacing adjustment algorithm for capture threshold testing provides a minimum pacing energy, e.g., about 3.5 volts, for patients with low capture thresholds, such as less than about 1 volt. For patients with high capture thresholds, setting the safety pacing energy to a predetermined value above the capture threshold provides an adequate stimulation level to ensure consistent capture.

A number of the examples presented herein involve block diagrams illustrating functional blocks used for in accordance with embodiments of the present invention. It will be understood by those skilled in the art that there exist many possible configurations in which these functional blocks can be arranged and implemented. The examples depicted herein provide examples of possible functional arrangements used to implement the approaches of the invention. The components and functionality depicted as separate or discrete blocks/elements in the figures in general can be implemented in combination with other components and functionality. The depiction of such components and functionality in individual or integral form is for purposes of clarity of explanation, and not of limitation. It is also understood that the components and functionality depicted in the Figures and described herein can be implemented in hardware, software, or a combination of hardware and software.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of operating a cardiac device, comprising:
delivering non-test pacing pulses to a heart in an automatic capture verification (ACV) mode during non-capture threshold test pacing therapy;
determining if loss of capture occurs while pacing during the ACV mode;
suspending the ACV mode if loss of capture occurs, otherwise maintaining the ACV mode;
determining if a capture threshold was acquired within a predetermined amount of time prior to suspension of the ACV mode;
if the capture threshold was acquired within the predetermined amount of time prior to the suspension of the ACV mode:
    initiating a safety pacing mode (SP) after suspension of the ACV mode; and
    delivering pacing pulses having a pacing energy that is based on the capture threshold energy during the SP mode;
if the capture threshold was not acquired within the predetermined amount of time prior to suspension of the ACV mode:
    initiating the SP mode after suspension of the ACV mode; and
    delivering pacing pulses having a pacing energy of a predetermined energy during the SP mode;
initiating a capture threshold test (CTT) mode during which primary pacing pulses and backup pacing pulses are delivered during cardiac cycles of the CTT mode;
determining if the ACV mode is active or non active at the time the CCT mode is initiated;
if the ACV mode is not active at the time the CCT mode is initiated, adjusting a pacing energy for backup pacing during the CTT mode based on the capture threshold energy used during the SP mode; and
if the ACV mode is active at the time the CCT mode is initiated, adjusting the pacing energy for the backup pacing during the CTT mode to a predetermined energy.

2. The method of claim 1, wherein:
the capture threshold comprises a capture threshold of a first heart chamber; and
one or both of the backup paces delivered during the CTT mode and the pacing pulses delivered during the SP mode are delivered to a second heart chamber.

3. A method of operating a cardiac device, comprising:
delivering non-test pacing pulses to a heart in an automatic capture verification (ACV) mode during non-capture threshold test pacing therapy;
determining if loss of capture occurs;
suspending the ACV mode if loss of capture occurs, otherwise maintaining the ACV mode;
determining if a capture threshold was acquired within a predetermined amount of time prior to suspension of the ACV mode;
if the capture threshold was acquired within the predetermined amount of time prior to suspension of the ACV mode:

initiating a safety pacing (SP) mode; and
delivering pacing pulses having a pacing energy that is based on the capture threshold energy during the SP mode;
if the capture threshold was not acquired within a predetermined amount of time prior to suspension of the ACV mode:
initiating the SP mode; and
delivering pacing pulses having a pacing energy of a predetermined energy during the SP mode.

4. The method of claim 3, wherein:
the capture threshold comprises a capture threshold of a first heart chamber; and
one or both of the backup paces delivered during the CCT mode and the pacing pulses delivered during the SP mode are delivered to a second heart chamber.

5. A method of operating a cardiac device, comprising:
delivering non-test pacing pulses to a heart in an automatic capture verification (ACV) mode during non-capture threshold test pacing therapy;
initiating a capture threshold test (CTT) mode during which a test pace and a backup pace are delivered for each cycle of a plurality of cardiac cycles of the CCT test mode;
determining if the ACV mode is active or non-active at the time the CTT mode is initiated;
determining if a capture threshold was acquired within a predetermined amount of time of initiating the CTT mode;
if the ACV mode is not active at the time the CTT mode is initiated and the capture threshold was acquired within the predetermined amount of time, adjusting a pacing energy for backup pacing during the CTT mode based on the capture threshold energy;
if the ACV mode is not active at the time the CTT mode is initiated and the capture threshold was not acquired within the predetermined amount of time, adjusting the pacing energy for backup pacing during the CTT mode to a first predetermined energy; and
if the ACV mode is active at the time the CTT mode is initiated, adjusting the pacing energy for the backup pacing during CTT mode to a second predetermined energy.

6. The method of claim 5, wherein:
the capture threshold comprises a capture threshold of a first heart chamber; and
the backup paces are delivered to a second heart chamber.

7. A method of operating a cardiac device, comprising:
pacing in an automatic capture verification (ACV) mode;
in response to loss of capture occurring during the ACV mode:
suspending the ACV mode; and
pacing in a safety pacing (SP) mode;
determining if a capture threshold has been acquired prior to suspension of the ACV mode; and
adjusting a pacing energy for the SP mode based on whether or not the capture threshold of has been acquired;
initiating a capture threshold test (CTT) mode during which a test pace and a backup pace are delivered for each of a plurality of cardiac cycles of the CTT mode;
determining if the ACV mode is active or non-active at a time the CTT mode is initiated; and
adjusting a pacing energy for backup paces delivered during the CTT mode based on whether or not the ACV mode is active or non-active at the time the CTT mode is initiated.

8. The method of claim 7, wherein:
the capture threshold comprises a capture threshold of a first heart chamber; and
the backup paces are delivered to a second heart chamber.

9. The method of claim 7, wherein:
the capture threshold comprises a capture threshold of a first heart chamber; and
paces delivered during the SP mode are delivered to a second heart chamber.

10. The method of claim 7, wherein determining if the capture threshold has been acquired comprises determining if the capture threshold has been acquired during a predetermined time prior to suspension of the ACV mode.

11. A medical device for delivering cardiac pacing therapy to a patient, comprising:
a plurality of electrodes configured to electrically couple to a heart;
capture threshold detection circuitry coupled to the electrodes and configured to determine a capture threshold;
pacing circuitry configured to deliver pacing pulses to the heart; and
control circuitry configured to:
deliver non-test pacing pulses to a heart in an automatic capture verification (ACV) mode during non-capture threshold test pacing therapy via the pacing circuitry;
suspend the ACV mode if loss of capture occurs, otherwise maintaining the ACV mode;
determine if a capture threshold was acquired within a predetermined amount of time prior to suspension of the ACV mode;
if the capture threshold was acquired within the predetermined amount of time prior to suspension of the ACV mode:
initiate a safety pacing mode (SP) after suspension of the ACV mode; and
deliver pacing pulses having a pacing energy based on the capture threshold energy during the SP mode;
if the capture threshold was not acquired within the predetermined amount of time prior to suspension of the ACV mode:
initiate the SP mode after suspension of the ACV mode; and
deliver pacing pulses having a pacing energy of a predetermined energy during the SP mode via the pacing circuitry;
initiate a capture threshold test (CTT) mode during which primary pacing pulses and backup pacing pulses are delivered for each cardiac cycle of the CTT mode;
determine if the ACV mode is active or non active at the time the capture threshold test is initiated;
if the ACV mode is not active at the time the capture threshold test is initiated, adjust a pacing energy for backup pacing during the CTT mode based on the capture threshold energy used during the SP mode; and
if the ACV mode is active, at the time the capture threshold test is initiated adjust the pacing energy for the backup pacing during the CTT mode to a predetermined energy.

12. The device of claim 11, wherein:
the capture threshold comprises a capture threshold of a first heart chamber; and
the backup paces are delivered to a second heart chamber.

13. The device of claim 11, wherein the pacing energy for backup pacing during the CTT mode is a multiple of the capture threshold energy used during the SP mode.

14. A medical device for delivering cardiac pacing therapy to a patient, comprising:
 a plurality of electrodes configured to electrically couple to a heart;
 capture threshold detection circuitry coupled to the electrodes and configured to determine a capture threshold;
 pacing circuitry configured to deliver pacing pulses to the heart; and
 control circuitry configured to:
  deliver non-test pacing pulses to a heart in an automatic capture verification (ACV) mode during non-capture threshold test pacing therapy via the pacing circuitry;
  determine if loss of capture occurs;
  suspend the ACV mode if loss of capture occurs, otherwise maintaining the ACV mode;
  determine if a capture threshold was acquired within a predetermined amount of time prior to suspension of the ACV mode;
  if the capture threshold was acquired within a predetermined amount of time prior to suspension of the ACV mode:
   initiate a safety pacing (SP) mode; and
   deliver pacing pulses having a pacing energy that is a multiple of the capture threshold energy during the SP mode via the pacing circuitry;
  if the capture threshold was not acquired within a predetermined amount of time prior to suspension of the ACV mode:
   initiate the SP mode; and
   deliver pacing pulses having a pacing energy of a predetermined energy during the SP mode via the pacing circuitry.

15. The device of claim 14, wherein:
 the capture threshold comprises a capture threshold of a first heart chamber; and
 one or both of the backup paces and the paces delivered during the SP mode are delivered to a second heart chamber.

16. The device of claim 15, wherein the first heart chamber comprises a left ventricle and the second heart chamber comprises a right ventricle.

17. A medical device for delivering cardiac pacing therapy to a patient, comprising:
 a plurality of electrodes configured to electrically couple to a heart;
 capture threshold detection circuitry coupled to the electrodes and configured to determine a capture threshold;
 pacing circuitry configured to deliver pacing pulses to the heart; and
 control circuitry configured to:
  deliver non-test pacing pulses to a heart in an automatic capture verification (ACV) mode during non-capture threshold test pacing therapy;
  initiate a capture threshold test (CTT) mode;
  determine if ACV mode is active or non active at the time the CCT mode is initiated;
  determine if a capture threshold was acquired within a predetermined amount of time;
  if the ACV mode is not active and the capture threshold was acquired within the predetermined amount of time, adjust a pacing energy for backup pacing during the CTT mode to a multiple of the capture threshold energy;
  if the ACV mode is not active and the capture threshold was not acquired within the predetermined amount of time, adjust the pacing energy for backup pacing during the CTT mode to a first predetermined energy; and
  if the ACV mode is active, adjust the pacing energy for the backup pacing during the CTT mode to a second predetermined energy.

18. The device of claim 17, wherein:
 the capture threshold comprises a capture threshold of a first heart chamber; and
 the backup paces are delivered to a second heart chamber.

19. The device of claim 18, wherein the first heart chamber comprises a right heart chamber and the second heart chamber comprises a left heart chamber.

20. A medical device for delivering cardiac pacing therapy to a patient, comprising:
 a plurality of electrodes configured to electrically couple to a heart;
 capture threshold detection circuitry coupled to the electrodes and configured to determine a capture threshold;
 pacing circuitry configured to deliver pacing pulses to the heart; and
 control circuitry configured to:
  pace the heart in an automatic capture verification (ACV) mode via the pacing circuitry;
  in response to loss of capture occurring during the ACV mode:
   suspend the ACV mode; and
   pace in a safety pacing (SP) mode after suspension of ACV;
   determine if a capture threshold has been acquired prior to suspension of the ACV mode; and
   adjust a pacing energy used during the SP mode based on whether or not the capture threshold of has been acquired;
  initiate a capture threshold test (CTT) mode during which a test pace and a backup pace are delivered for each of a plurality of cardiac cycles of the CTT mode;
  determine if the ACV mode is active or non-active at the time the CTT mode is initiated; and
  adjust a pacing energy for backup paces delivered during the CTT mode based on whether or not the ACV mode is active or non-active at the time the CTT mode is initiated.

21. The device of claim 20, wherein:
 the capture threshold comprises a capture threshold of a first heart chamber; and
 the backup paces or are delivered to a second heart chamber.

22. The device of claim 20, wherein:
 the capture threshold comprises a capture threshold of a first heart chamber; and
 paces delivered during the SP mode are delivered to a second heart chamber.

23. The device of claim 22, wherein the first heart chamber is a right ventricle and the second heart chamber is a left ventricle.

24. The device of claim 20, wherein the control circuitry is further configured to determine if the capture threshold has been acquired during a predetermined time prior to suspension of the ACV mode.

25. A system for operating a cardiac device, comprising:
 a plurality of electrodes configured to electrically couple to a heart;
 capture threshold detection circuitry coupled to the electrodes and configured to determine a capture threshold;
 pacing circuitry configured to deliver pacing pulses to the heart; and
 means for initiating a capture threshold test (CTT) mode, determining if an automatic capture verification (ACV) mode is active at the time the CTT mode is initiated, adjusting a pacing energy for backup pacing during the CTT mode based on the capture threshold energy if the ACV mode is not active at the time the CTT mode is initiated, and adjusting the pacing energy for the backup pacing during the CTT mode to a predetermined energy if the ACV mode is active at the time the CCT mode is initiated.

26. A system for operating a cardiac device, comprising:
a plurality of electrodes configured to electrically couple to a heart;
capture threshold detection circuitry coupled to the electrodes and configured to determine a capture threshold;
pacing circuitry configured to deliver pacing pulses to the heart; and
means for delivering non-test pacing pulses to a heart in an automatic capture verification (ACV) mode during non-capture threshold test pacing therapy, suspending the ACV mode and initiating a safety pacing (SP) mode if loss of capture occurs, determining if a capture threshold was acquired within a predetermined amount of time prior to suspension of the ACV mode, if the capture threshold was acquired within the predetermined amount of time prior to suspension of the ACV mode, delivering SP mode pacing pulses having a pacing energy that is based on the capture threshold energy, or if the capture threshold was not acquired within a predetermined amount of time prior to suspension of the ACV mode, delivering SP mode pacing pulses having a pacing energy of a predetermined energy.

* * * * *